United States Patent
Fleming et al.

[19]

[11] Patent Number: 6,106,488

[45] Date of Patent: Aug. 22, 2000

[54] FLEXURAL RIGIDITY PROFILE GUIDEWIRE TIP

[75] Inventors: Thomas E. Fleming, Plymouth; Jeffrey H. Vogel, Brooklyn Park; Anthony Kelzenberg, Watertown, all of Minn.

[73] Assignee: SciMed Life Systems, Inc., Maple Grove, Minn.

[21] Appl. No.: 09/132,379

[22] Filed: Aug. 11, 1998

[51] Int. Cl.[7] .................................................. A61B 5/00
[52] U.S. Cl. ............................................................. 600/585
[58] Field of Search ................................... 600/434, 435, 600/585

[56] References Cited

U.S. PATENT DOCUMENTS

| | | | |
|---|---|---|---|
| 4,721,117 | 1/1988 | Man et al. | 600/585 |
| 5,433,200 | 7/1995 | Fleishhacker | 600/585 |
| 5,497,783 | 3/1996 | Urick et al. | 600/585 |
| 5,520,194 | 5/1996 | Migata et al. | 600/585 |
| 5,551,444 | 9/1996 | Finlayson | 600/585 |

OTHER PUBLICATIONS

Declaration of Jeffrey H. Vogel in Accordance with 37 CFR §1.132 and Exhibit 1.

*Primary Examiner*—Max Hindenburg
*Attorney, Agent, or Firm*—Crompton, Seager & Tufte, LLC

[57] ABSTRACT

A guidewire having an intermediate flexibility region to provide trackability and steerability while reducing guide catheter device back out. In one embodiment, the guidewire includes a distal flexibility region, intermediate flexibility region and proximal flexibility region. The intermediate or support flexibility region preferably extends from between about 3 cm to 40 cm proximally of the distal tip. The intermediate region is divided into at least two sections of varying stiffness.

12 Claims, 3 Drawing Sheets

FLEXURAL RIGIDITY PROFILE GUIDEWIRE TIP

FIELD OF THE INVENTION

The present invention pertains generally to the field of guidewires. More particularly, the present invention pertains to the flexibility of guidewires.

BACKGROUND OF THE INVENTION

Guidewires have come into widespread use as devices for delivering diagnostic or therapeutic medical devices through body lumens such as a patient's vasculature. In the field of coronary angioplasty, for example, guidewires are generally advanced through a femoral artery access point, through a guiding catheter to reach the ostium of a coronary artery and through the coronary artery to a lesion or clog in the coronary artery. A therapeutic device such as an angioplasty catheter can then be advanced over the guidewire to the lesion. The lesion can be dilated by the angioplasty catheter to improve blood flow through the vessel. To prevent rebound or reclosing of the dilated vessel, a stent can be advanced over the guidewire on a balloon delivery catheter and placed across the dilated lesion.

A typical guidewire for performing angioplasty is at least about 135 cm long. Such a wire generally has a distal tip region extending approximately 7 cm from the distal tip. The distal tip region is generally soft enough to be considered atraumatic. The guidewire typically has an intermediate region extending from about 7 to 35 cm proximally from the distal tip. This region is stiffer than the distal region. The remaining proximal region of the guidewire is usually stiffer yet than the intermediate region.

The intermediate region of the guidewire must be flexible enough to be steerable into a patient's coronary arteries. However, those guidewires having highly flexible intermediate regions are prone to being pulled out or displaced from the coronary arteries when the relatively stiff therapeutic catheters are advanced over them. This is particularly true when a stent and a stent delivery catheter are advanced over such a guidewire.

Conversely, those guidewires having a substantially stiffer intermediate section are not readily steerable into a patient's coronary arteries. When placed, these relatively stiff guidewires tend to straighten curved arteries by placing pressure on the wall of a vessel lumen. When the guidewire is pressed against the wall of the vessel lumen, it becomes more difficult to advance a therapeutic or diagnostic device over the guidewire.

SUMMARY OF THE INVENTION

The present invention pertains to an improved guidewire having a flexibility which provides good steerability and torqueability while limiting pull out or displacement of the guidewire and guiding catheter. In one embodiment, the guidewire includes a distal flexibility region, intermediate flexibility region and proximal flexibility region. The intermediate or support flexibility region preferably extends from between about 7 cm to 35 cm proximally of the distal tip. The intermediate region is divided into at least two sections of differing stiffness.

In a preferred embodiment, the guidewire includes an elongate core wire having a proximal end and a distal end. The core wire has a proximal region, an intermediate region and a distal region. At least a portion of the intermediate region is disposed between about 7 cm and about 25 cm proximally of the distal end. A covering member, such as a coil spring or a polymer sleeve, is disposed around a substantial portion of the intermediate region of the core wire.

The flexural rigidity of the guidewire at the portion of the intermediate region of the guidewire is greater than at the distal region and less than at the proximal region. The guidewire has at least two sections of differing flexural rigidity at the portion of the intermediate region of the core wire. The more proximal of the two sections of flexural rigidity has a flexural rigidity of about 1.5 to about 3.0 times more than the more distal of the two intermediate sections. More preferably, the more proximal of the two sections of flexural rigidity has a flexural rigidity of about 1.8 to about 2.5 times more than the more distal of the two sections.

In an alternate embodiment, the guidewire includes more than two sections of flexible rigidity at the intermediate region of the core wire. In this embodiment, the stiffest section of the more than two sections has a flexural rigidity of about 1.5 to about 3.0 times the least stiff of the more than two sections. More preferably, however, the stiffest section of the more than two sections of flexural rigidity has a flexural rigidity of about 1.8 to about 2.5 times more than the least stiff of the more than two sections. In one embodiment, the core wire itself includes the various sections described above with respect to the guidewire assembly as a whole.

DETAILED DESCRIPTION OF THE INVENTION

Figure 1:
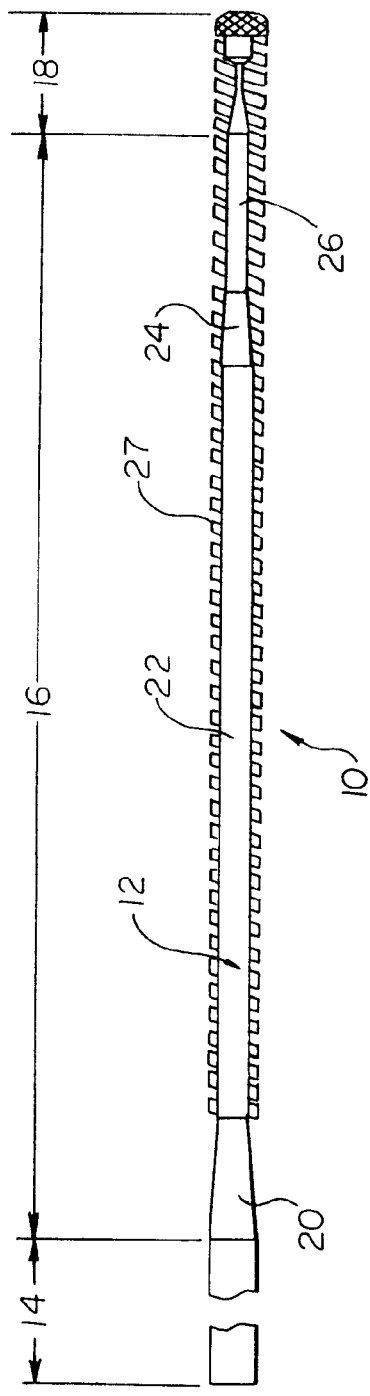
FIG. 1 is a side view of a guidewire in accordance with the present invention.

Referring now to the drawings wherein like reference numerals refer to like elements throughout the several views, FIG. 1 is a side view of a guidewire 10 in accordance with the present invention. Guidewire 10 includes a core wire 12 having a proximal region 14, an intermediate region 16 and a distal region 18. Core wire 12 is preferably stainless steel, but can be made from Nitinol or other biocompatible material. Guidewire 10 has a proximal end and distal end and a length between the ends of at least 135 cm if the wire is intended to reach the coronary artery by femoral artery access. Guidewire 10 can also be considered to have a proximal region, intermediate region and distal region generally corresponding in position with the proximal, intermediate and distal regions of core wire 12. If the guidewire is an exchange wire for reaching the coronary arteries, the guidewire would have a length of about 300 cm. The length of the intermediate region is preferably between about 15 to 40 cm, and more preferably between about 20 and about 30 cm. Distal region 18 is preferably 0 to 15 cm in length and, more preferably, between 7 to 12 cm in length. Thus, the intermediate region would begin and extend proximally from about 0 to 15 cm from the distal end or, more preferably, from about 7 to 12 cm from the distal end of guidewire 10.

Proximal region 14 is preferably coated with a layer of PTFE to provide enhanced lubricity. Lubricity aids in the advancement and withdrawal of the guidewire, and advancement and withdrawal of therapeutic and diagnostic devices over the guidewire. Proximal region 14 preferably has a diameter of about 0.011 inches to about 0.017 inches and, more preferably, from about 0.012 inches to 0.014 inches, and most preferably, about 0.013 inches.

Intermediate region 16 preferably has a reduced diameter relative to the diameter of proximal region 14. In an exemplary embodiment, intermediate region 16 can include a first distal tapering portion 20 having a length of approximately 1.0 to 3.5 cm. Distally of taper 20 is a constant diameter portion 22 having a diameter of preferably about 0.010 inches and length of about 16.5 cm. Intermediate region 16 can include a second taper 24 having a length of approximately 3 cm and a second constant diameter portion 26 having a length of approximately 8 cm and a diameter of approximately 0.008 inches.

A substantial portion of intermediate region 16, and distal region 18 is surrounded by a covering member 27 which is shown in FIG. 1 in cross section as a helical coil. The coil shown in FIG. 1 can be soldered to core wire 12, or otherwise attached to core wire 12 in a manner known to those skilled in the art. Furthermore, alternative coverings can be placed over core wire 12, rather than a coil. For example, as disclosed by Burmeister et al., in U.S. Pat. No. 5,452,726 a polymer can be disposed over the intermediate region 16 and distal region 18. U.S. Pat. No. 5,452,726 to Burmeister et al. is incorporated herein by reference.

Figure 2:
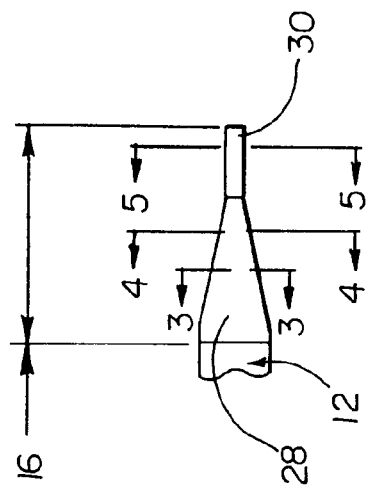
FIG. 2 is a detail of a distal region of the core wire of the guidewire of FIG. 1.

FIG. 2 is a detail of distal region 18 of core wire 12. A third taper 28 extends distally of the distal end of intermediate region 16 and is a proximate portion of distal region 18. A flat ribbon portion 30 extends distally from taper 28. If a coil will be soldered to core wire 12, wire 12 can include a heat sink disposed distally of ribbon 30. In an exemplary embodiment of guidewire 10, taper portion 28 is approximately 8.0 cm in length. Ribbon portion 34 is approximately 2 cm in length.

Figure 3:
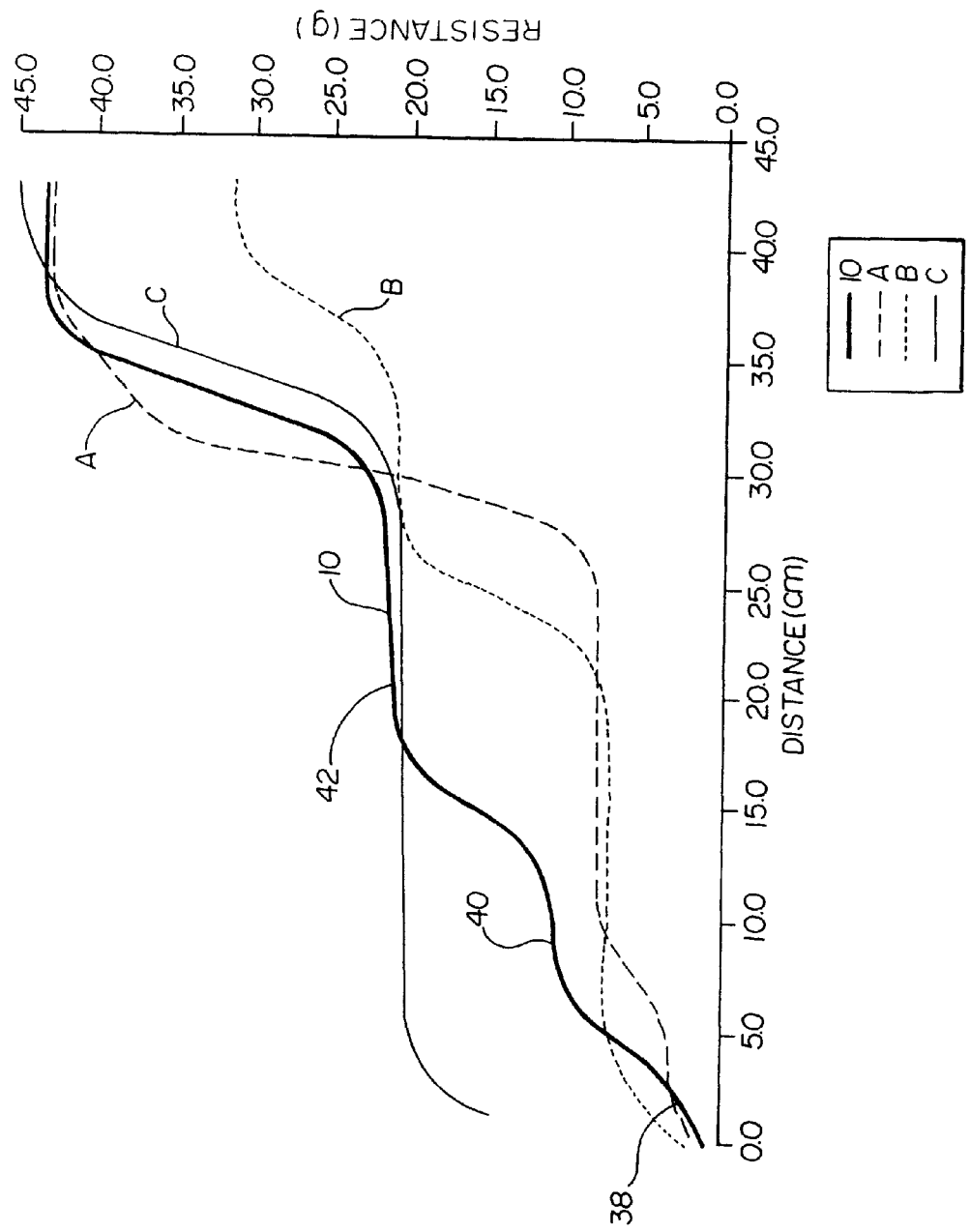
FIG. 3 is a graph of the flexibility of a guidewire in accordance with the present invention relative to the guidewire's distal end, plotted against flexibility data for various other guidewires.

FIG. 3 is a graph of guidewire flexural rigidity, measured as the load required in grams to create a certain deflection of the guidewire. The graph of the flexibility versus distance from the distal end is plotted for four guidewires including guidewire 10 of the present invention as described above with respect to FIGS. 1–5 and three representative prior art guidewires A, C and B. (A is a guidewire marketed by Advanced Cardiovascular Systems, Inc. under the trademark Hi-Torque Floppy II™. B is a guidewire marketed by Advanced Cardiovascular Systems, Inc. under the trademark Hi-Torque Balance Middle Weight™ and C is a guidewire marketed by Advanced Cardiovascular Systems, Inc. under the trademark Hi-Torque Extra S'port™.) The distal end of intermediate region 16 begins approximately 10 cm from the distal end of guidewire 10 and extends approximately about 25 cm.

The flexibility of the guidewire at a given location is best described in terms of properties that are relatively easy to measure, for example, the diameter of a core wire cross section and the elastic (Young's) modulus E of the material or materials. If the wire is composed of a single material, flexibility can be defined as the inverse of the product of the moment of inertia I of the cross section with respect to the bending axis and the Young's modulus E. The product EI is known in scientific literature as the "flexural rigidity" of the beam. For a round wire with single material the moment of inertia I is $\pi d^4/64$, where d is the diameter of the wire. Accordingly, the flexural rigidity is then:

$$EI = \pi E d^4/64$$

This defines flexibility of a wire at a point. Thus, if EI is doubled the wire is said to be twice as stiff.

When the core wire is surrounded by a spring coil, the contribution of the coil to the guidewire flexural rigidity can generally be neglected. If the wire has uniform flexibility or flexural rigidity over some distance, then the wire's flexibility can be measured somewhat more directly than by the above formula. By holding one end of the uniform section fixed, applying a known weight or force perpendicular to the wires axis at the other end of the uniform section, the deflection from the original straight axis will be proportional to the flexibility, i.e., inversely proportional to the flexural rigidity of the wire. The deflection will also be proportional to the force or weight applied, as well as the cube of the length tested. Thus, the deflection corresponding to a known load or the force required to cause a known deflection, can be used as a direct measure of the wire's flexibility or flexural rigidity for cases where the flexibility is uniform over a sufficient length.

Figure 4:
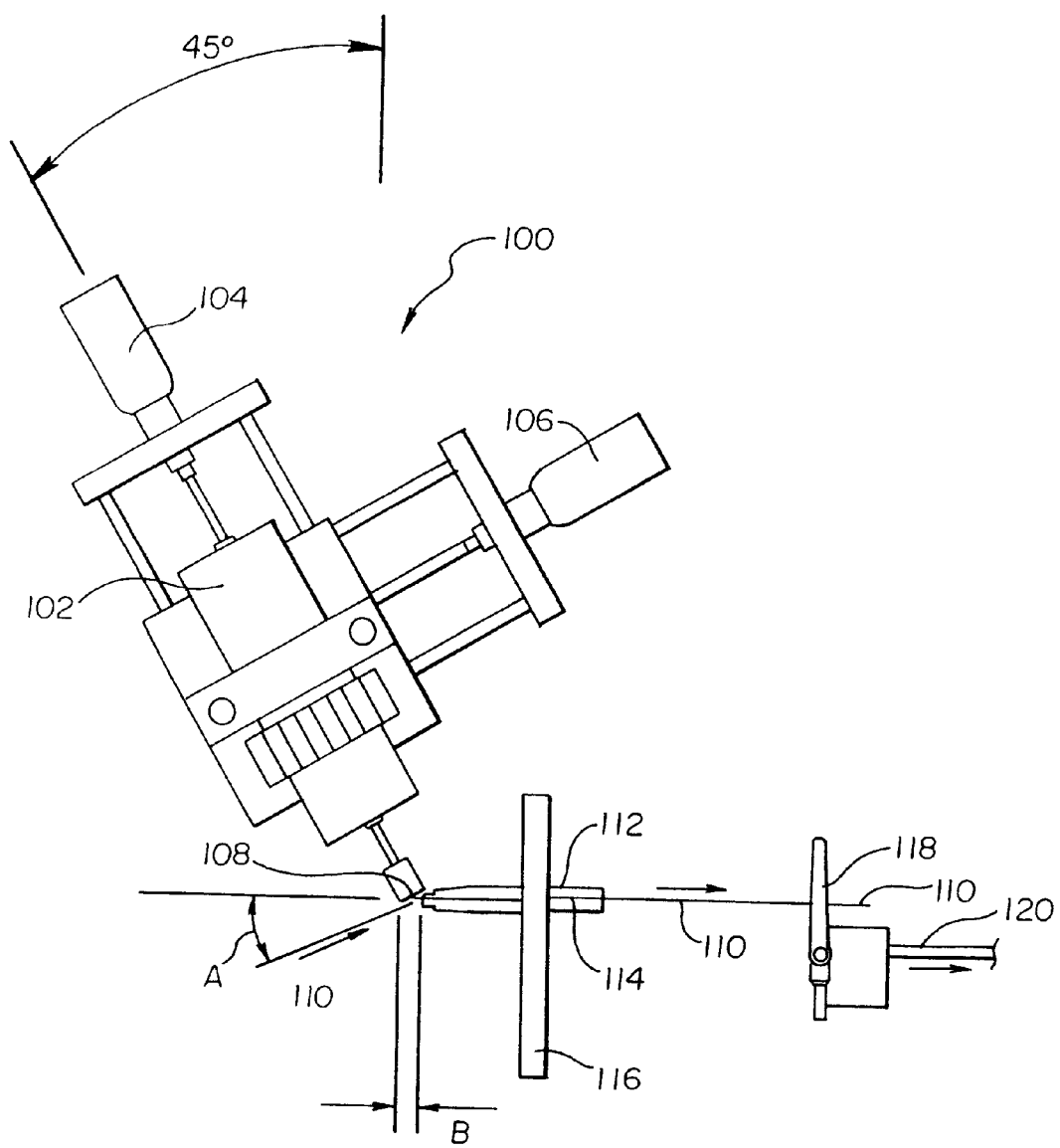
FIG. 4 is a schematic view of a flexibility tester.

FIG. 4 is a schematic view of a flexibility tester 100 for determining the flexural rigidity in grams of a guidewire. Flexibility tester 100 includes a force transducer which is preferably a Lucas, Schaevitz transducer Model No. FTD-G-50, connected to a force pin 108, which is adjustable axially by a force dial 104 and transversely by a distance dial 106. Flexibility tester 100 and force pin 108 are preferably disposed at 45° to vertical. A guidewire 110 is disposed in a wire guide 112 having a wire guide lumen 114 having an inside diameter of 0.016 inches extending therethrough. Wire guide 112 is fixed in place by support 116. A wire clamp 118 is releasably connected to guidewire 110. Clamp 118 is connected to a drive rod 120 which can be connected to a solenoid or other means to move clamp 118 and guidewire 110 to the right at a controlled rate.

Force pin 108 preferably has a diameter of 0.025 inches and is preferably spaced a distance B of 0.25 inches from wire guide 112. Angle A between the longitudinal axis of wire guide lumen 114 and the portion of wire 110 extending to the left therefrom, is a constant during flexibility testing. As wire 110 is drawn to the right by clamp 118 through guide 112, if the flexibility of wire 110 varies, the force necessary to maintain a constant angle A will also vary. The variation in force will be detected by force transducer 102 which is preferably connected to a computer plotter or similar device to record the variation in force. Plots such as the one shown in FIG. 3 can be created by recording the resistance or force in grams measured by transducer 102 relative to the distance along a guidewire.

Force tester 100 is calibrated by advancing a 0.013 inch diameter straightened 304 stainless steel alloy test mandrel through wire guide 112. Force transducer 102 is advanced such that force exerted by pin 108 creates a constant angle A when force transducer reads 45 grams at a nominal constant wire speed of 3 inches per minute to the right.

The graph of FIG. 3 was arrived at using this direct method of measuring flexible rigidity described with respect to FIG. 4. Thus, the graph is only substantially accurate in those regions where the flexibility is uniform of the tested length, those regions are shown on the graph as substantially horizontal lines. These portions correspond to constant diameter sections of a guidewire's core wire.

As shown in FIG. 3, guidewire 10 is shown to have an intermediate region having dual support sections 40 and 42. The less rigid section 40 corresponds to the 0.008 inch constant diameter portion 26. The stronger intermediate support section 42 corresponds to the 0.01 constant diameter portion 22. Section 40 provides enhanced support inside the coronary arteries or a vein graft relative to wires A and B. Whereas section 40 has enhanced steerability or flexibility over guidewire C. Section 42 provides additional support over guidewires B and C to decrease the likelihood of "back out" of the guidewire and guiding catheter when a stiff balloon catheter or stent delivery system turns into a sharp bend off the left main or right coronary artery. A section 38 provides a soft generally atraumatic distal tip region.

It is particularly desirable that a substantial portion of the dual support sections 40 and 42 are disposed between 10 to about 35 cm proximally of the distal end of guidewire 10. Preferably, section 42 has a flexural rigidity of about 1.5 to about 3.0 times more than section 40. More preferably, section 42 has a flexural rigidity of about 1.8 to about 2.5 times greater than the flexural rigidity of section 40. It should be understood that guidewire 10 can have additional sections of flexibility in the intermediate section 16. These can include taper portions or additional incrementally stepping constant diameter portions. The flexural rigidity of section 42 is preferably 15 to 25 grams, as measured on tester 100, and more preferably, 17.5 to 22.5 grams, as measured on tester 100, and most preferably, about 21 grams, as measured on tester 100. The flexural rigidity of section 40 is preferably 5 to 15 grams, and more preferably 7.5 to 12.5 grams, as measured on tester 100 and most preferably about 11 grams, as measured on tester 100.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A guidewire comprising:
an elongate core wire having a proximal end and a distal end, the core wire having a proximal region, an intermediate region and a distal region, at least a portion of the intermediate region being disposed between about 7 cm and about 25 cm proximally of the distal end; and
a covering member disposed around a substantial portion of the intermediate region of the core wire, wherein the flexural rigidity of the guidewire at the portion of the intermediate region of the guidewire is greater than at the distal region and less than at the proximal region, and the guidewire has at least two sections of differing flexural rigidity at the portion of the intermediate region of the core wire, the more proximal of the two sections of flexural rigidity having a flexural rigidity of about 1.5 to about 4 times more than the more distal of the two intermediate sections.

2. The guidewire in accordance with claim 1, wherein the more proximal of the two sections of flexural rigidity has a flexural rigidity of about 2.0 to about 2.5 times more than the more distal of the two sections.

3. The guidewire in accordance with claim 1, wherein the guidewire includes more than two sections of flexural rigidity at the intermediate region of the core wire, and the stiffest section of the more than two sections has a flexural rigidity of about 1.5 to about 3.0 times the least stiff of the more than two sections.

4. The guidewire in accordance with claim 3, wherein the stiffest section of the more than two sections of flexural rigidity has a flexural rigidity of about 2.0 to 2.5 times more than the least stiff of the more than two sections.

5. A guidewire core wire, comprising:
an elongate wire having a proximal end and a distal end, the wire having a proximal region, an intermediate region and a distal region, at least a portion of the intermediate region being disposed between 7 cm and 25 cm proximally of the distal end; and
wherein the flexural rigidity of the wire at the intermediate region is greater than at the distal region and less than at the proximal region, and the intermediate region of wire has at least two sections of differing flexural rigidity the more proximal of the two sections of flexural rigidity having a flexural rigidity of about 1.5 to about 3.0 times more than the more distal of the two sections.

6. The core wire in accordance with claim 5, wherein the more proximal of the two sections has a flexural rigidity of about 2.0 to about 2.5 times more than the more distal of the two sections.

7. The core wire in accordance with claim 5, wherein the core wire includes more than two sections of differing flexibility at the intermediate region, and the stiffest of the more than two sections has a flexural rigidity of about 1.5 to about 3.0 times the least stiff of the more than two sections.

8. The core wire in accordance with claim 7, wherein the stiffest of the more than two sections has a flexural rigidity of about 2.0 to about 2.5 times more than the least stiff of the more than two sections.

9. A guidewire comprising:
an elongate core wire having a proximal end and a distal end, the core wire having a proximal region, an intermediate region and a distal region, at least a portion of the intermediate region being disposed between about 7 cm and about 35 cm proximally of the distal end; and
a covering member disposed around a substantial portion of the intermediate region of the core wire, wherein the flexural rigidity of the guidewire at the portion of the intermediate region of the guidewire is greater than at the distal region and less than at the proximal region, and the guidewire has at least two sections of differing flexural rigidity at the portion of the intermediate region of the core wire, the more proximal of the two sections of flexural rigidity having a flexural rigidity of about 1.5 to about 3 times more than the more distal of the two intermediate sections.

10. The guidewire in accordance with claim 9, wherein the more proximal of the two sections of flexural rigidity has a flexural rigidity of about 2.0 to about 2.5 times more than the more distal of the two sections.

11. The guidewire in accordance with claim 9, wherein the guidewire includes more than two sections of flexural rigidity at the intermediate region of the core wire, and the stiffest section of the more than two sections has a flexural rigidity of about 1.5 to about 3.0 times the least stiff of the more than two sections.

12. The guidewire in accordance with claim 11, wherein the stiffest section of the more than two sections of flexural rigidity has a flexural rigidity of about 2.0 to 2.5 times more than the least stiff of the more than two sections.

* * * * *